United States Patent [19]

Tihon et al.

[11] Patent Number: 5,356,423
[45] Date of Patent: Oct. 18, 1994

[54] RESECTABLE SELF-EXPANDING STENT

[75] Inventors: Claude Tihon, Eden Prairie; John H. Burton; Bradford G. Staehle, both of Minnetonka, all of Minn.; Michael A. Mikulich, La Conversion, Switzerland

[73] Assignee: American Medical Systems, Inc., Minnetonka, Minn.

[21] Appl. No.: 53,846

[22] Filed: Apr. 22, 1993

Related U.S. Application Data

[63] Continuation of Ser. No. 875,675, Apr. 29, 1992, abandoned, which is a continuation-in-part of Ser. No. 637,356, Jan. 4, 1991, abandoned.

[51] Int. Cl.$^5$ .................... A61M 29/00; A61F 2/06
[52] U.S. Cl. ........................ 606/194; 623/1; 623/12
[58] Field of Search ............... 623/1, 11, 12; 606/191, 606/192, 193, 194, 195, 196–200; 600/36

[56] References Cited

U.S. PATENT DOCUMENTS

| | | | |
|---|---|---|---|
| 4,655,771 | 4/1987 | Wallsten | 623/1 |
| 4,776,337 | 10/1988 | Palmaz | 623/1 |
| 4,878,906 | 11/1989 | Lindemann et al. | 623/1 |
| 4,879,135 | 11/1989 | Greco et al. | 623/1 |
| 4,893,623 | 1/1990 | Rosenbluth | 606/192 |
| 4,954,126 | 9/1990 | Wallsten | 623/1 |
| 4,957,479 | 9/1990 | Roemer | 604/8 |
| 4,957,508 | 9/1990 | Kaneko et al. | 623/1 |
| 5,015,253 | 5/1991 | MacGregor | 623/1 |

FOREIGN PATENT DOCUMENTS

| | | | |
|---|---|---|---|
| 0201466 | 11/1986 | European Pat. Off. | 623/1 |
| 1602513 | 12/1970 | France . | |
| 2189150A | 10/1987 | United Kingdom | 623/1 |

*Primary Examiner*—David Isabella
*Assistant Examiner*—Debra S. Brittingham
*Attorney, Agent, or Firm*—Haugen and Nikolai

[57] ABSTRACT

A stent for transluminal implantation comprising a single-piece tubular member having a fenestrated side wall exhibiting a pattern of uniformly spaced openings defined by intersecting strands where the strands are integrally joined together at their points of intersection whereby the tubular member can be radially compressed from a larger diameter to a smaller diameter by the application of a uniform inwardly directed radial force and which self-expands to a larger diameter when the radial compressive force is removed. The compression and subsequent self-expansion occurs without an appreciable change in the stent's length. By forming the stent from a thermoplastic material, it may later be resected by carving it up into small pieces preferably using an electrosurgical instrument.

10 Claims, 2 Drawing Sheets

RESECTABLE SELF-EXPANDING STENT

CROSS-REFERENCE TO RELATED APPLICATION

This application is a continuation of application Ser. No. 07/875,675, filed Apr. 29, 1992, now abandoned, which is a continuation-in-part of application Ser. No. 07/637,356, filed Jan. 4, 1991, now abandoned.

BACKGROUND OF THE INVENTION

I. Field of the Invention

This invention relates generally to stent devices of the type intended to be inserted in tubular body organs for maintaining the organ in a patent condition, and more particularly to the design of a tubular stent whose thermoplastic material and geometry allow it to expand by itself from a radially compressed condition to a larger diameter and which can later be resected using an electrosurgical instrument.

II. Discussion of the Prior Art

Various forms of surgical stents are known in the art for maintaining a tubular body organ, such as a vein, artery, bile duct, fallopian tube or urethra, in a patent condition whereby body fluids can continue to flow in a normal fashion. Consider the condition termed benign prostatic hypertrophy where, in the male urinary system, with age, the prostate gland may swell. If the urethra which the gland surrounds is collapsed to the point where the flow or urine from the bladder becomes partially or even fully blocked, surgical intervention is often required. In surgically addressing this problem, a transurethral resection of the prostate is often performed in which portions of the prostate gland are shaved or resected away using an electrosurgical instrument called a resectoscope.

Another approach in treating an enlarged prostate involves inserting a dilatation catheter into the urethra and advancing that catheter until the balloon portion thereof is aligned with the prostate. Then the balloon is inflated to stretch and enlarge the urethra. Another treatment involves the insertion of a stent which functions to re-enforce the urethra at the site so that the tissue involved does not collapse to obstruct urine flow.

Where a stent is to be implanted transurethrally, it is an important characteristic that it possess a low cross-sectional profile to facilitate its being routed to the desired site within the urethra. Once appropriately positioned, it is desirable that the stent expand to a larger diameter and that it remain stable at that diameter over an extended period to provide the necessary support for inhibiting the urethra from again collapsing. Various devices having this property are described in the patent art. For example, in U.S. Pat. No. 4,655,771 to Wallsten, there is described a tubular stent formed from braided metal wire which, when stretched longitudinally, will assume a relatively small diameter, but when it is allowed to spring back to a shorter length, an attendant increase in the diameter takes place. This device suffers from a number of practical problems, not the least of which is the difficulty in properly positioning the stent so that, when released, it will collapse longitudinally and increase in size radially to the point where patency is established along the length of the prostate without having a portion of the stent protrude into the external sphincter so as to result in urinary incontinence or, alternatively, into the bladder where it would serve as a nidus for stone formation.

Moreover, if only a short length stent is called for, there is a tendency for the individual wires comprising the stent to unbraid. Thus, this type of stent may not be usable following a TURP procedure to support only the portion of the urethra at the neck of the bladder. Yet another drawback is that the free ends of the braided wire stent have projecting whiskers that can irritate the lining of the vessel in which it has been implanted.

Also, if a stent of the type described in the Wallsten patent remains in the body for a period of several months, tissue ingrowth occurs and the stent, because of its open construction, becomes incorporated into the vessel wall where it is shielded from the urine. However, should it become necessary to explant the stent for any reason, it becomes extremely difficult to remove it through the urethra.

The Rosenbluth U.S. Pat. No. 4,893,623 describes a tubular stent where the wall of the tube is slit in a predetermined fashion. To implant the stent, it is mounted over a deflated balloon on a dilatation catheter and then routed to the appropriate site in the tubular organ where the stent is to be deployed. The stent is made from a malleable metal so that, when the balloon is inflated, it will stretch the walls of the stent, creating an open lattice pattern. When the balloon is again deflated, the stent will remain stretched to the diameter established by the inflated balloon and the dilatation catheter can again be withdrawn from the body.

The stent arrangement described in the Rosenbluth patent also becomes difficult to remove once tissue ingrowth has occurred. Moreover, it is not self-expanding but, instead, must be stretched to a desired diameter through the application of an outward radial force. When that outside force is removed, the stent does not provide a residual outward radial force against the vessel wall. This may lead to undesired migration of the stent within the hollow vessel subsequent to its implantation and prior to the establishment of tissue ingrowth.

OBJECTS

It is accordingly a principal object of the present invention to provide an improved tubular stent for use in the lumen of a tubular body organ.

Another object of the invention is to provide a tubular stent which may readily be resected from a tubular body organ at a later time if deemed necessary.

Yet another object of the invention is to provide a self-expanding tubular stent which is capable of being inserted through the lumen of a tubular body organ while in a radially compressed state exhibiting a small diameter, but which is self-expanding to a larger diameter upon being released from its insertion tool without exhibiting a significant length change and which continues to exert a residual outward radial force against the vessel wall to maintain the stent in place.

A further object of the invention is to provide a tubular stent fabricated from a thermoplastic material, which is self-expanding and which is capable of being resected by being cut into pieces with an electrosurgical instrument.

SUMMARY OF THE INVENTION

The foregoing features, objects and advantages of the invention are achieved by providing a one-piece, non-braided stent for insertion into the lumen of a tubular body organ for maintaining that lumen in a patent condition. The stent preferably consists of a thermoplastic tubular member of generally circular cross-section having a pattern of openings formed through the wall to effectively create a pattern of intersecting strands which are coplanar at their points of intersection allowing the member to be radially compressed from a larger diameter to a smaller diameter without undergoing any appreciable elongation and which can then expand when the radial compressive force is removed. Because it is preferably fabricated from a thermoplastic material, it and any ingrown tissue can move relative to one another at their junction points such that these strands cannot be shaved or resected into smaller pieces for later removal should that become necessary. By controlling the electrical conductivity of the thermoplastic material so that it approximates that of human tissue, the ability to resect the stent using an electrosurgical instrument is enhanced.

As indicated above, the stent of the present invention comprises a non-braided thermoplastic web or mesh formed into a closed tube where the web or mesh includes a pattern of apertures of a predetermined shape defined by strands which are integrally joined at their points of intersection. This allows the closed tube to be radially compressed from a relatively larger diameter to a significantly smaller diameter when subjected to inward radially directed compressive forces uniformly applied over its surface, but which returns to a predetermined intermediate diameter when those compressive forces are removed. Unlike the prior art stent shown in Wallsten U.S. Pat. No. 4,655,771, the radial compression and expansion is not accompanied by an attendant change in length because the intersecting strands defining the pattern of apertures being integrally joined are constrained from angularly shifting or moving relative to one another at their points of intersection. The intermediate diameter is sufficiently large to assure continuing outward force against the lumen wall. This tends to prevent unwanted migration prior to the time that tissue ingrowth occurs. A particularly efficacious device has been found to result when a pattern of openings defined by thin strands of an acetal homopolymer thermoplastic resin where the radial thickness of the strands are about $1\frac{1}{4}$–$2\frac{1}{4}$ times their circumferential width. With this pattern, the fenestrated tube may be radially compressed from a larger diameter, $d_1$, to a smaller diameter, $d_2 = d_1/4$. The ability of the stent to spring back to a predetermined outer diameter depends upon the degree of plastic deformation that the material undergoes as well as the amount of creep encountered. Acetal homopolymers exhibit good creep resistance and dimensional stability.

Being a plastic having a relatively low melting point, the stent of the invention can be electrosurgically resected. It is also substantially easier to trim to a desired length or shape prior to or subsequent to implantation. Doing so does not result in the formation of sharp whisker-like stubs at the cut end of the stent as does a braided wire stent.

The features and advantages as well as the method of making and using the tubular stent of the present invention will become apparent to those skilled in the art from the following detailed description of a preferred embodiment, especially when considered in conjunction with the accompanying drawings in which numerals in the several views refer to corresponding parts.

DESCRIPTION OF THE PREFERRED EMBODIMENT

Figure 1:
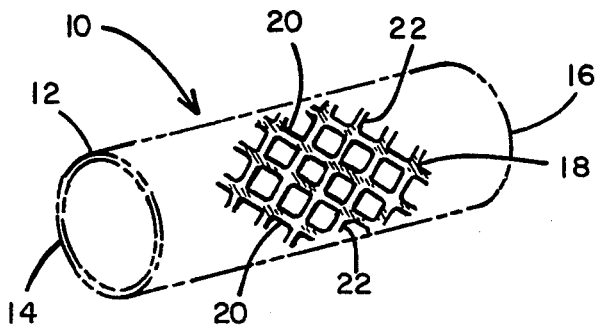
FIG. 1 is a greatly enlarged perspective view of a self-expanding tubular stent in accordance with the present invention.

With reference to FIG. 1, the self-expanding intraluminal prosthesis or stent is identified generally by numeral 10 and is seen to include a generally tubular member 12 having a pair of opposed ends 14 and 16 and a fenestrated wall surface 18. The stent of FIG. 1 may be formed in a molding operation or, alternatively, may be created from a solid tube by laser or water-jet cutting the pattern of apertures so as to leave non-woven, non-braided intersecting thread-like strips as at 20 and 22 therebetween. It is to be noted that the strips are integrally joined in the same plane rather than overlapping one another as with a braided stent.

The material from which the stent 10 is formed is preferably a thermoplastic having a high modulus of elasticity such that when it is subjected to inwardly directed radial forces uniformly applied over its surface, it will collapse to a lesser diameter but then spring back when the radial compressive forces are removed. A variety of medical-grade plastics are available which exhibit a high modulus of elasticity and which may be employed in fabricating the self-expanding stents of the present invention. For example, nylon or a suitable polyester or acetal homopolymer may be used.

Various manufacturing methods are available for fabricating the stent in accordance with this invention. Prototypes have been produced by appropriately mounting a solid tube of plastic on a mandrel and then, using a laser, the fenestrations or apertures are cut through the thickness dimension of the wall, leaving a plurality of coplanar intersecting strands creating contiguous rhombic apertures. The intersecting strands are integrally joined at their points of intersection and, hence, are precluded from moving or shifting relative to one another at their union. With no particular limitation intended, each of the individual strands 20, 22 may be 0.015 in. thick in the radial direction and 0.010 in. wide in the circumferential direction. The laser may be computer-controlled, insuring accurate spacing and precise line definition.

In a production setting, it is contemplated that the stents of the present invention may be formed in a molding operation which results in very low-cost production in comparison to the laser cutting method.

Figure 2:
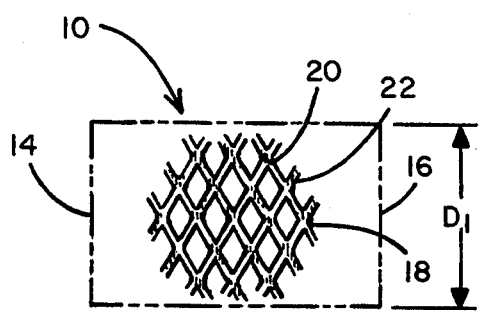
FIG. 2 is a side elevation view of the stent of FIG. 1 at the time of manufacture and prior to being loaded into the stent delivery device.
Figure 3:
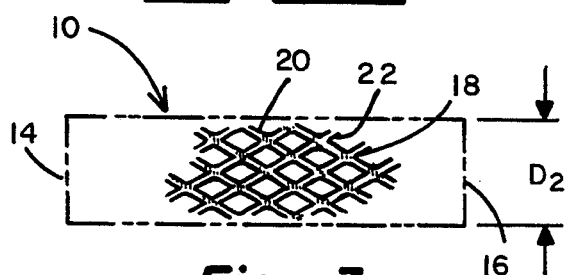
FIG. 3 is a side elevation view of the stent of FIG. 1 when radially compressed for insertion into the lumen of a tubular body organ.
Figure 4:
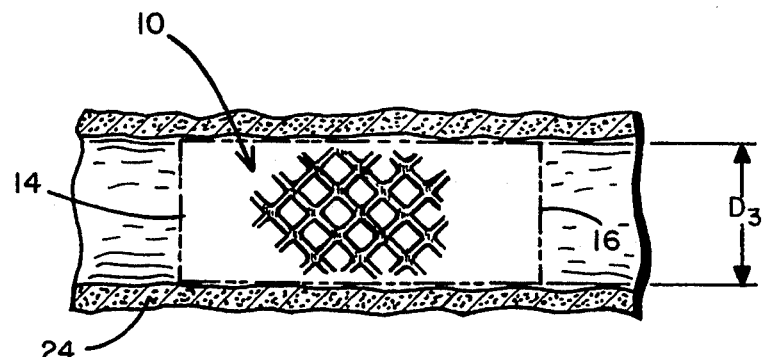
FIG. 4 is a side elevation view of the stent of FIG. 1 following release from its insertion tool.

Referring next to FIGS. 2 through 4, at the time of manufacture, the diameter of the stent 10 is purposely oversized compared to the size of the lumen in which it is intended ultimately to be implanted. For example, it may be designed to initially have an outside diameter, $d_1$, as shown in FIG. 2. Prior to insertion into the lumen of the hollow body organ to be supported, the stent of FIG. 2 is radially compressed into an insertion tool and will collapse as shown in FIG. 3 to exhibit a significantly lower diameter, $d_2$. When the tool and stent have been routed through the body lumen to the location where the stent is to be placed, it is released from the tool and allowed to expand to an intermediate diameter, $d_3$, which is less than diameter, $d_1$, (due to plastic deformation) sufficient to still provide support to the walls of the tubular organ which, in FIG. 4, is identified by numeral 24.

Figure 6:
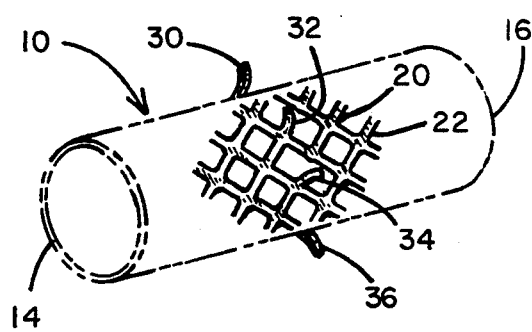
FIG. 6 is a side elevation of the invention illustrating a variation including tissue engaging hook elements.

While collapsing the stent to its smallest diameter, $d_2$, (FIG. 3) results in some measure of plastic deformation, by originally over-sizing the stent as shown in FIG. 2, it is capable of self-expansion to a working diameter, $d_3$, as shown in FIG. 4. In fact, the stent is preferably designed such that when in position within the body organ, it will continue to exert a slight outward force against the internal walls of the body organ, thus tending to maintain the stent in position and reducing the tendency of the stent to migrate. Alternatively, appropriately disposed, radially-projecting finger-like barbs may be incorporated to resist such migration. Such a stent is depicted in FIG. 6. With the barbs centrally disposed on the stent, there is less tendency for the stent to migrate than if the barbs extend from one of the stent's ends.

By loading the stent of FIG. 2 into its insertion tool and thereby reducing its size to that shown in FIG. 3, immediately prior to the implantation thereof, creep deformation, which is time dependent, is minimized.

Figure 7:
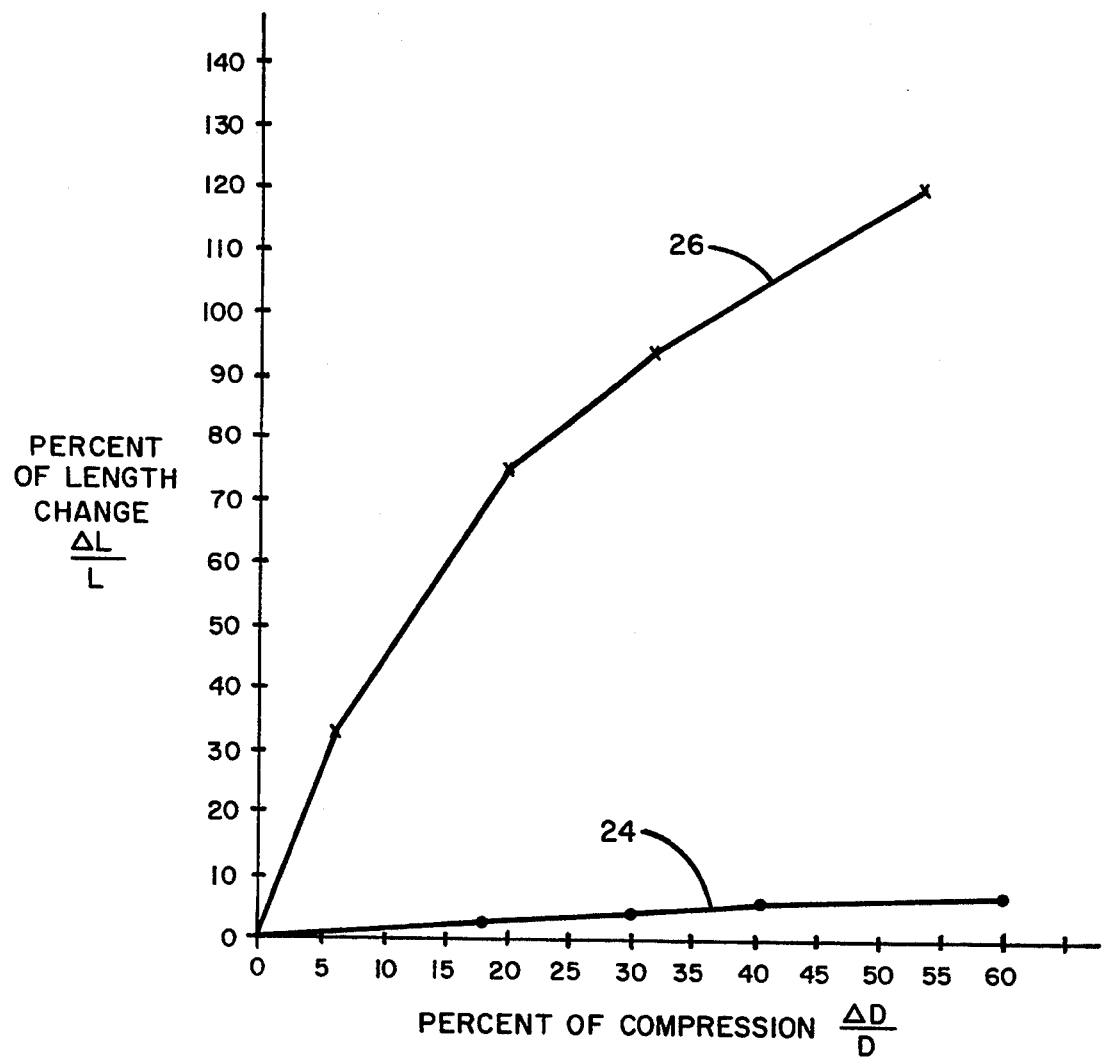
FIG. 7 is a plot showing the difference in elongation of the stent of the present invention with radial compression compared with a braided stent.

FIG. 7 illustrates by means of a graph the change in length of the stent of the present invention with changes in stent diameter (curve 24) as contrasted to a braided metal stent made by applicants' assignee in accordance with the aforereferenced Wallsten U.S. Pat. No. 4,655,771 and sold under the trademark, UROLUME, (curve 26). As is indicated by the curves, a 50% reduction in diameter due to radial compression of the stent of the present invention results in a length change of less than 10% and more particularly, approximately 5%. A corresponding reduction in diameter of the UROLUME stent results in a length change of about 115%. Thus, if the dimension $d_1$ is 10 mm and it is compressed down to a dimension $d_2$ of 5 mm (a 50% reduction), a stent originally 26 mm long would lengthen to 27.3 mm whereas in the case of the UROLUME stent, it would lengthen from 26 mm to 55.9 mm. When contrasted to the prior art Wallsten-type stent, then, the one of the present invention can be said to have no significant change in length upon either radial compression or radial expansion. This fact become very important when accurate positioning of the stent in a tubular body vessel is required.

Figure 5:
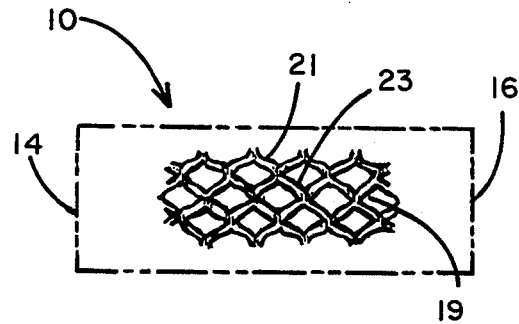
FIG. 5 is a side elevation view of a stent having a pattern of apertures whose shape enhances the self-expanding characteristics of the device.

In the stent shown in FIG. 1, the openings are shaped like a rhombus. Good results have been achieved when the acute angles thereof are in the range of from 40° to 60° such that the corresponding obtuse angles fall into the range of from 140° to 120°. Computer analysis has shown that this shape results in a concentration of stress forces at the points of intersection of the strands where they are integrally joined. By shaping the openings as shown in the stent of FIG. 5, the stress concentration points are significantly reduced. The apertures or openings in FIG. 5 may be described as those which result when the strands defining those openings have a sinusoidal pattern and where the negative peaks of a first strand are integrally joined to the positive peak of an adjacent strand. Because the apertures resemble the eye opening of a human, for ease in description, they are referred to herein as eye-shaped apertures. Because the intersecting strands remaining following the effective removal of the material comprising the apertures are integrally joined at their points of intersection, the opposed ends of the stent are free of sharp points which occur when a braided tube structure of the type disclosed in the Wallsten patent is cut to a desired length. Hence, the stent of the present invention is less traumatic to tissue at the time of its implantation. Moreover, being fabricated from a material like DELRIN ® plastic, it can readily be trimmed to a desired length or end-shape configuration by the surgeon at the time of implantation or later.

By forming the stent of the present invention from a suitable thermoplastic material and by introducing an additive to the material, its electrical conductivity can be made comparable to that of the tissue in which the stent will become embedded. Should it become necessary or desirable to later remove the stent device, an appropriate electrosurgical instrument may be used to cut through both the involved tissue and the stent material so that the pieces resulting can be withdrawn through the body lumen in which the stent had been positioned. The heating produced by the electrosurgical instrument when sufficient to cut through tissue will also have the ability to cut through the plastic strands comprising the stent of the present invention. The fact that the conductivity of the tissue and the stent material are approximately the same results in greater uniformity and control of the electrosurgical current as the resection takes place. Not only can the conductivity characteristics of the plastic stent material be modified, but it is also contemplated that certain drugs can be incorporated on or in the material for subsequent slow-release into adjacent tissue or into the bloodstream, depending upon the site of the stent implant.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A stent for insertion into a tubular organ for maintaining the organ patent, comprising a single-piece, single-layer, non-braided tubular member having a single-plane fenestrated side wall exhibiting a pattern of regular cut-outs forming spaced openings, said tubular member radially compressible from a larger diameter to a smaller diameter and self-expandable when the radial compressive force is removed, the compression and later expansion producing a change in length of less than about 10%.

2. The stent as in claim 1 wherein said tubular member is formed from an electrosurgically resectable material.

3. The stent as in claim 2 wherein said electrosurgically resectable material is a thermoplastic.

4. The stent as in claim 3 wherein said resectable material is an acetal homopolymer thermoplastic resin.

5. The stent as in claim 3 wherein said thermoplastic material incorporates a slow-release chemical component therein.

6. The stent as in claim 2 wherein said electrosurgically resectable material has an electrical conductivity approximately that of body tissue.

7. The stent as in claim 1 wherein said openings are generally parallelogram shaped.

8. The stent as in claim 1 wherein said openings are generally eye-shaped.

9. The stent as in claim 1 wherein a radial compression of said tubular member by fifty percent results in a change in length of less than ten percent.

10. The stent as claimed in claim 1 wherein the tubular member has a radial thickness from about 1.25 to 2.25 times the smallest distance between the spaced openings.

* * * * *